(12) United States Patent
Zhang et al.

(10) Patent No.: US 6,214,297 B1
(45) Date of Patent: Apr. 10, 2001

(54) HIGH VOLTAGE PULSE GENERATOR

(75) Inventors: Qinghua Howard Zhang, Columbus, OH (US); Xiangxlao Qiu, Ottawa (CA)

(73) Assignee: The Ohio State University, Columbus, OH (US)

(*) Notice: Subject to any disclaimer, the term of this patent is extended or adjusted under 35 U.S.C. 154(b) by 0 days.

(21) Appl. No.: 09/275,313

(22) Filed: Mar. 24, 1999

(51) Int. Cl.$^7$ .................................................. B01J 19/08
(52) U.S. Cl. ......................... 422/186; 435/173.1; 99/451
(58) Field of Search ........................ 422/186; 435/173.1; 99/451

(56) References Cited

U.S. PATENT DOCUMENTS

| | | | |
|---|---|---|---|
| 3,876,373 | 4/1975 | Glyptis | 21/54 |
| 4,524,079 | 6/1985 | Hofmann | 426/234 |
| 4,695,472 | 9/1987 | Dunn et al. | 426/237 |
| 4,750,100 | * 6/1988 | Ragsdale | 363/86 |
| 4,838,154 | 6/1989 | Dunn et al. | 99/451 |
| 5,048,404 | 9/1991 | Bushnell et al. | 99/451 |
| 5,235,905 | 8/1993 | Bushnell et al. | 99/451 |
| 5,250,160 | 10/1993 | Oksman et al. | 204/131 |
| 5,282,940 | 2/1994 | Griffis et al. | 204/131 |
| 5,290,583 | 3/1994 | Reznik et al. | 426/614 |
| 5,393,541 | 2/1995 | Bushnell et al. | 426/237 |
| 5,415,882 | 5/1995 | Knipper et al. | 426/237 |
| 5,447,733 | 9/1995 | Bushnell et al. | 426/237 |
| 5,514,391 | 5/1996 | Bushnell et al. | 426/237 |
| 5,527,105 | 6/1996 | Riach, Jr. | 312/406 |
| 5,534,278 | 7/1996 | De Ruyter et al. | 426/237 |
| 5,549,041 | * 8/1996 | Zhang et al. | 99/451 |
| 5,562,024 | 10/1996 | Polny, Jr. | 99/451 |
| 5,603,972 | 2/1997 | McFarland | 426/240 |
| 5,607,710 | 3/1997 | De Ruyter et al. | 426/237 |
| 5,630,360 | 5/1997 | Polny, Jr. | 99/451 |
| 5,662,031 | * 9/1997 | Quin et al. | 99/451 |
| 5,690,978 | 11/1997 | Yin et al. | 426/237 |
| 6,043,066 | * 3/2000 | Mangano et al. | 435/173.7 |
| 6,087,863 | * 7/2000 | Aflatouni | 327/411 |

OTHER PUBLICATIONS

"Engineering Aspects of Pulsed Electric Field Pasteurization," Zhang, Qinghua, et al., Journal of Food Engineering, 25:261–281, 1994. No month available.

"Inactivation of *E. Coli* and *S. Cerevisiae* by Pulsed Electric Fields Under Controlled Temperature Conditions," Zhang, Q., et al., 1994 American Society of Agricultural Engineers, vol. 37 (2): 581–587, No month available.

"Inactivation of Microorganisms in a Semisolid Model Food Using High Voltage Pulsed Electric Fields," Zhang, Quinghua, et al., Food Science & Technology (1wt), 1994, 27 (6) : 538, No month available.

* cited by examiner

Primary Examiner—Kishor Mayekar
(74) Attorney, Agent, or Firm—Nenad Pejic Calfee, Halter & Griswold LLP (57) ABSTRACT

The present invention provides a high-voltage pulse generation system particularly suited for Pulsed Electric Field (PEF) treatment of food products. The system includes, for example, a power source, an energy storage component in circuit communication with the power source and for storing energy from the power source, a plurality of switches for opening and closing periodically to discharge the energy storage component, and a load comprising at least one Pulse Electric Field (PEF) treatment chamber in which biological cells are subjected to PEF treatment. The power source charges energy storage component and a trigger device appropriates triggers the opening and closing of the switches. The switches may arranged in any one of a number of configurations including, for example, an H-bridge switch configuration where the load is in circuit communication with the switches through the bridge portion of the H-bridge. Additionally, a plurality of energy storage component arrangements are also disclosed.

17 Claims, 5 Drawing Sheets

HIGH VOLTAGE PULSE GENERATOR

Federal sponsorship of this invention has been provided by Contract No. DAAK60-95C-2064 awarded by the U.S. Army.

FIELD OF THE INVENTION

The present invention relates to methods and systems for generating high-voltage pulses. More particularly, the present invention relates to the design of a PEF treatment system for generating high-voltage bipolar and/ or unipolar pulses used to induce stress and mortality in biological cells.

BACKGROUND OF THE INVENTION

PEF technology has found a wide range of applications in different areas such as, for example, bio-fouling control, non-thermal food processing, odor control, and NOx removal. Extensive research has been conducted to study the efficacy of using PEF as a non-thermal food pasteurization/ sterilization method. However, the application of PEF treatment is not straightforward due to a number of factors. Factors affecting PEF treatment include, for example, electric field strength, treatment temperature, stage of microbial growth, and total treatment time.

In typical PEF treatment systems, high voltage pulses are induced in food products by specially designed PEF treatment chambers. Fluid food products are primarily conductive due to the existence of charge carrying particles such as, for example, proteins, vitamins and minerals. Therefore, application of a high-voltage across a treatment chamber results in a large flux of current flowing through the food product. This same current must also flow through the high-voltage pulse generator that is generating the high-voltage pulse(s).

In this regard, a PEF treatment chamber generally has two electrodes that convert high-voltage pulses to pulsed electric fields. Food product residing in between the electrodes is exposed to this field. For effective treatment, the design of the treatment chamber should guarantee a uniform field distribution inside the treatment zone. However, due to the large contact area between the two electrodes, the resistance therebetween is typically small and often in the range of half an Ohm to a couple of Ohms. Consequently, it is difficult for conventional high-voltage pulse generators to drive a PEF treatment chamber that has such a small resistance.

Accordingly, conventional high-voltage pulse generators are disadvantageous for a number of reasons. One disadvantage is that few high-voltage pulse generators can maintain the extremely high currents required due to the low resistances of treatment chambers. Additionally, conventional high-voltage pulse generators only provide for unipolar pulses that cause the deposition of protein and other charge carrying particles on electrodes. Therefore, methods and apparatuses for providing high-voltage pulses that do not suffer from these and other disadvantages are desirable.

SUMMARY OF THE INVENTION

According to the present invention, methods and systems for generating high-voltage unipolar or bipolar pulses for inducing changes in biological cells is provided. The methods and systems are particularly suited for the pasteurization and/or sterilization of, but not limited to, pumpable food products. In accordance with present invention, a power source charges an energy storage component, either a capacitor or a pulse forming network (PFN). The particular composition of the energy storage component also influences the shape of high-voltage pulse that is applied (ie., substantially square pulse, exponential decay pulse, etc.) Multiple switches that are in circuit communication with the energy storage component are closed and then opened periodically to discharge the energy storage component. The switches are preferably controlled by a trigger control system. The periodical discharges result in application of high-voltage pulses to the load, where specially designed treatment chambers are connected, exposing biological cells inside treatment chambers to intense electric field(s). A high-voltage pulse transformer is preferably connected between the switches/energy storage component and the treatment chambers, to allow the switches to operate at different voltage and current levels or to operate with other desired features. Repetitive application of short duration, intense electric fields induces stress or mortality in biological cells which results in the inactivation of food-borne spoilage and pathogenic micro-organisms.

According to one embodiment of the present invention, a system for generating high-voltage bipolar pulses to induce stress and mortality in biological cells is provided. The system includes, for example, a power source, an energy storage component in circuit communication with the power source and for storing energy from the power source, a plurality of switches for opening and closing periodically to discharge the energy storage component, and a load comprising at least one Pulse Electric Field (PEF) treatment chamber in which biological cells are subjected to PEF treatment. The system may additionally include, for example, a pulse transformer in circuit communication with the energy storage component and the load and for allowing a plurality of voltage and current levels to be generated at the load. The energy storage component include, for example, at least one capacitor such that the energy storage component has a discharge time constant that is larger than the time interval between the closing and opening of the switches.

According to a second embodiment of the present invention, a system for generating high-voltage bipolar pulses to induce stress and mortality in biological cells is provided with an H-bride switching configuration. The system includes, for example, a power source, an energy storage component in circuit communication with the power source and for storing energy from the power source, a plurality of switches for opening and closing periodically to discharge the energy storage component which are configured in an H-bridge configuration, and a load comprising at least one Pulse Electric Field (PEF) treatment chamber in which biological cells are subjected to PEF treatment. The load is preferably in circuit communication with the switches through a bridge portion of the H-bridge configuration.

It is therefore an advantage of the present invention to provide a high-voltage pulse generator system for effective PEF treatment that generates bipolar and/or unipolar high-voltage pulses.

It is a further advantage of this invention to provide a high-voltage pulse generator system for effective PEF treatment that reduces or eliminates protein build-up on PEF treatment electrodes.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

DETAILED DESCRIPTION OF ILLUSTRATED EMBODIMENT

PEF treatment systems typically employ high-voltage pulses to induce stress and mortality in biological cells. One such PEF treatment system is disclosed in U.S. Pat. No. 5,690,978 to Yin el al. which is hereby fully incorporated by reference. The present invention provides a bipolar high-voltage pulse characteristic that reduces and/or eliminates the migration of charge carrying particles in the food product, such as proteins, from migrating in the direction of the electric field and depositing on one electrode—as occurs in typical unipolar PEF treatment systems. This migration of charge carrying particles has been known to cause local field distortions between the treatment electrodes and leads to arcing and non-uniform PEF treatment. Additionally, the present invention provides a switching circuit which is capable of maintaining high currents and/or voltages through small resistive loads, such as PEF treatment chambers.

Figure 1:
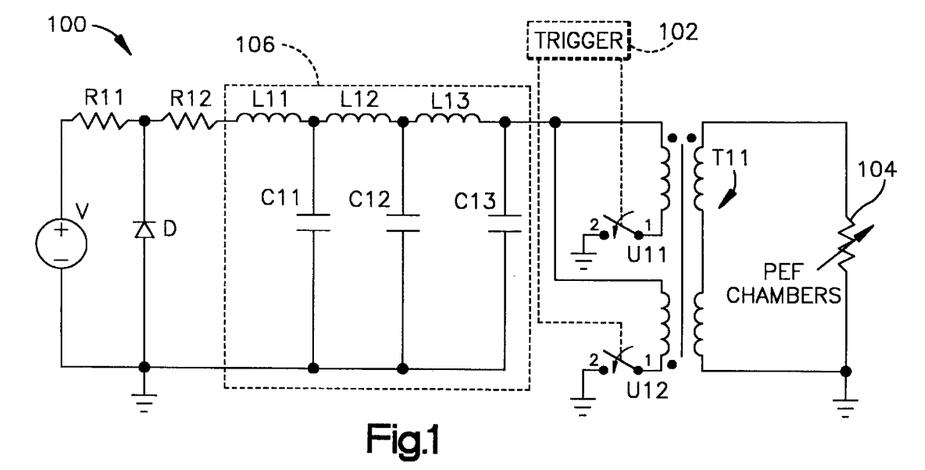
FIG. 1 is the schematic diagram of a first embodiment of a high voltage bipolar pulse generator.

FIG. 1 shows a circuit diagram 100 of a high-voltage bipolar pulse generator, including a power source V, an energy storage component 106 having inductors L11, L12, L13 and capacitors C11, C12, and C13, a set of switches U11 and U12, transformer T11, and a load 104 having one or more PEF treatment chambers. The power source V of circuit 100 is a DC power source, which can be any one of the following: an AC system with a rectifier and a regulator, conmmercial DC power supply, capacitor charging power supply, resonant charging system or any system that can provide desired voltage and energy levels. Two charging resistors R11 and R12 and a protective diode D are optionally shown for the purpose of isolation and protection.

The energy storage component 106 shown in FIG. 1 is a pulse forming network (PFN). The number of capacitor-inductor combinations (e.g, L11 and C11, L12 and C12, and L13 and C13), as well as the values of the capacitors and inductors used are dependent on specific design characteristics (i.e., pulse duration, amplitude, etc.) and are calculated and selected to suit. During the energy storage component 106 charging period, the capacitors thereof are charged up to the line voltage of the power source V.

A set of two switches U11 and U12 are closed periodically to discharge the energy storage component 106. Each time, only one switch is closed and involved in discharging the PFN while the other switch remains open. The switches U11 and U12 are preferably switching devices which are normally open and only close upon actuation such as, for example, thyratrons. The PFN controls, through trigger device 102, the discharge of energy and assists in opening the switches again till energy stored in PFN is transferred to a load 104 of PEF treatment chambers and current passing through the switch decreases to zero. The switches U11 and U12 are preferably grounded and, therefore, the corresponding driving circuits do not need to be floated at operating voltage. In all embodiments, the switches U11 and U22 are triggered by trigger device 102. The trigger device 102 is preferably a signal generator configured to generate a low-voltage square wave control signal of particular frequency "f", voltage, and duty ratio including time between pulses "dt" and pulse duration "τ". However, switches U11 and U12 may also be triggered by a computer control system, such as a PEF treatment master control system, configured with particular frequency, voltage, and duty ratios. Additionally, the waveform characteristics can be manually set or adjusted, or set or adjusted in real-time or by computer control based on a feedback system regulating the entire PEF treatment process. Additionally, in all embodiments, the load 104 includes at least one PEF treatment chamber and preferably between 2 to 8 PEF treatment chambers.

In the embodiment of FIG. 1, a high-voltage pulse transformer T11 and PEF treatment chambers form the load 104 of the pulse generator. The periodical discharges of the switches U11 and U12 apply pulses to two primary windings of the transformer T11. The PEF treatment chambers are connected to the secondary winding of the high-voltage pulse transformer T11. The transformer T11 serves as an isolation and control device. Therefore, the voltage and current levels experienced by the PEF treatment chambers can be different from the levels at the primary side of the transformer T11. For example, a low-voltage power source could be used with a step-up transformer to provide high-voltage pulses across the PEF treatment chambers, or a high-voltage power supply with a step-down transformer can be used to generate a lower-voltage at the PEF treatment chambers. Therefore, the current level at the primary side of the transformer can be many times smaller than the current passing through the PEF treatment chambers connected to the secondary side of the transformer. The terminals of the transformer T11 are preferably arranged as shown in FIG. 1. When the set of switches U11 and U12 are closed alternately, pulses of the same polarity are applied to the primary windings of the transformer T11 in alternate fashion resulting in bipolar pulses across the PEF treatment chambers. When only one of the switches is involved in the discharge, high-voltage unipolar pulses, either positive or negative in polarity, are generated across the PEF treatment chambers. Different types of waveforms can be generated using the system shown in FIG. 1. For example, by changing the energy storage component 106 to a pure capacitor bank, exponential decay pulses that are either bipolar and/or unipolar are generated and applied to the PEF treatment chambers. However, the preferred waveform is a substantially square pulse waveform.

Figure 2:
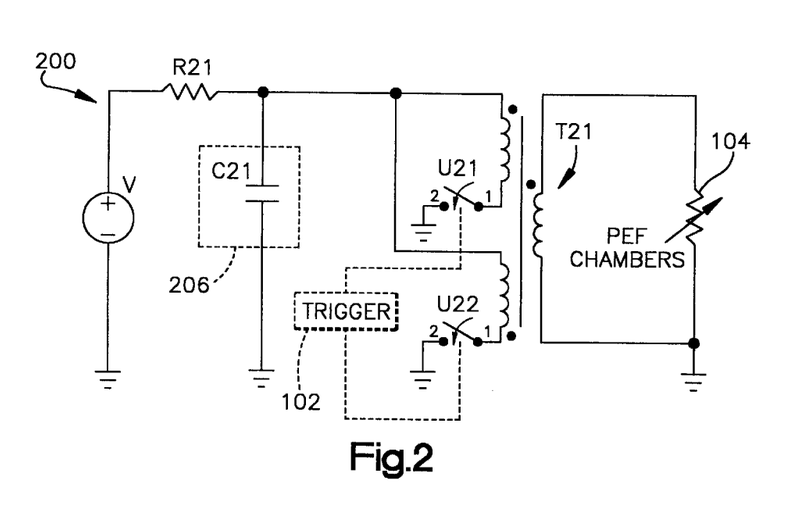
FIG. 2 is the schematic diagram of a second embodiment of a high voltage bipolar pulse generator.

Referring now to FIG. 2, a second embodiment 200 of a high-voltage bipolar pulse generator having a power source V, a resistive element R21, an energy storage component 206, a set of two switches U21 and U22, a transformer T21, and a load 104 having at least one PEF treatment chamber is shown. The power source V is similar to the power source used in FIG. 1. A capacitor C21 is used as the energy storage component 206. The power source V charges the energy storage capacitor C21 during a charging period. The two switches U21 and U22 are periodically closed for a short period of time to discharge the energy storage capacitor and then opened. As described above, each time only one switch is involved in discharging the capacitor C21 while the other switch remains open. Switches U21 and U22 are similar to switches U11 and U12 in that they are normally open and are actuated by a control signal. Suitable switching devices include, for example, CROSS-TRON, TETRODE, POWER MOSFET, IGBT, GATE-TURN-OFF SCRs or other switches with switching characteristics that meet the above-described requirements.

A high-voltage pulse transformer T21 and PEF treatment chambers form the load 104 of the system. The PEF treatment chambers are connected to the secondary windings of transformer 21. The terminals of the transformer's primary windings are preferably arranged and connected as shown in FIG. 2. When the two switches U21 and U22 alternately discharge capacitor C21, pulses are applied to the two primary windings of the pulse transformer T21. As described above, high-voltage bipolar pulses are generated at the secondary winding of transformer T21 and are applied to the PEF treatment chambers. Also as described above, when only one of the switches is involved in the discharge, high-voltage unipolar pulses, either positive or negative in polarity, are generated across the PEF treatment chambers.

To generate square wave pulses, the capacitance of the energy storage capacitor C21 is selected so that a discharge time constant of the circuit shown in FIG. 2 is comparably larger than the time interval between the closing and the opening of the switches U21 and U22. When the switch closing and opening time intervals are larger than five times the discharge time constant, exponential decay pulses are generated and applied to the PEF treatment chambers.

Figure 3:
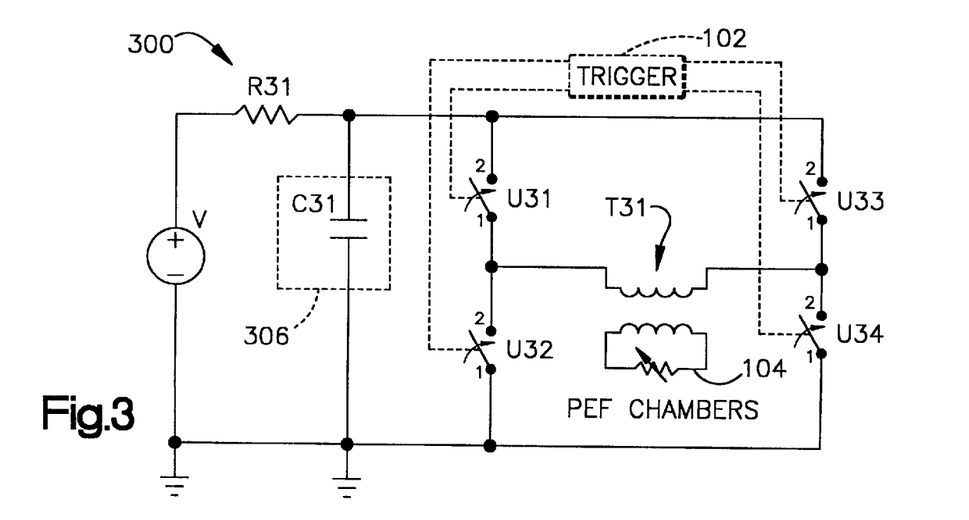
FIG. 3 is the schematic diagram of a third embodiment of a high voltage bipolar pulse generator.

Referring now to FIG. 3, a third embodiment 300 of a high-voltage bipolar pulse generator system is shown. The system has a power source V, resistive element R31, an energy storage component 306, a set of four switches U31, U32, U33, and U34, a transformer T31, and a load 104 having one or more PEF treatment chambers. The power source V and energy storage capacitor C31 are similar to the power source and energy storage capacitor C21 of FIG. 2. The power source V charges the energy storage capacitor R31 during the charging periods. The set of four switches U31, U32, U33, and U34 are arranged in an H-bridge switch configuration with transformer T31. The load 104 of PEF treatment chambers is in circuit communication with the switches through a bridge portion of the H-bridge configuration. The switches U31, U32, U33, and U34 comprise the same types of switching devices as those already described in connection with the embodiments of FIGS. 1–3.

The four switches operate in pairs, U31 and U34 are a pair and U32 and U33 are another pair. When a pair of switches is opened or closed, the two switches that comprise the pair are opened and closed at the same time. The two pairs of switches are closed and open periodically to discharge the energy storage capacitor C31. However, each time only one pair of switches is closed while the other pair remains open. In this manner, the pair of switches in each leg of the H-bridge (i.e., U31–U32 and U33–U34) could never be closed at the same time.

A high voltage pulse transformer T31 and PEF treatment chambers form the load 104 of the system. The PEF treatment chambers are connected to the secondary windings of the transformer T31. When the pairs of switches (e.g., U31–U34 and U32–U34) discharge capacitor C31 alternatively, pulses were applied to the primary winding of the pulse transformer T31. As a result thereof, high-voltage bipolar pulses are generated at the secondary winding of the transformer T31 and are applied to the PEF chambers.

To generate square wave pulses, the capacitance of the energy storage capacitor C1 should be selected such that a discharge time constant of the circuit shown in FIG. 3 is comparably larger than the time intervals between the closing and the opening of the pairs of switches. When they time intervals are larger than five times the discharge time constant, exponential decay pulses are generated and applied to the PEF treatment chambers. If only one pair of switches are closed and opened all the time, high voltage unipolar pulses, positive or negative in polarity, are generated. As described above, when only one pair of switches is involved in the discharging procedure, high-voltage unipolar pulses, either positive or negative in polarity, are generated across the PEF treatment chambers.

Figure 4:
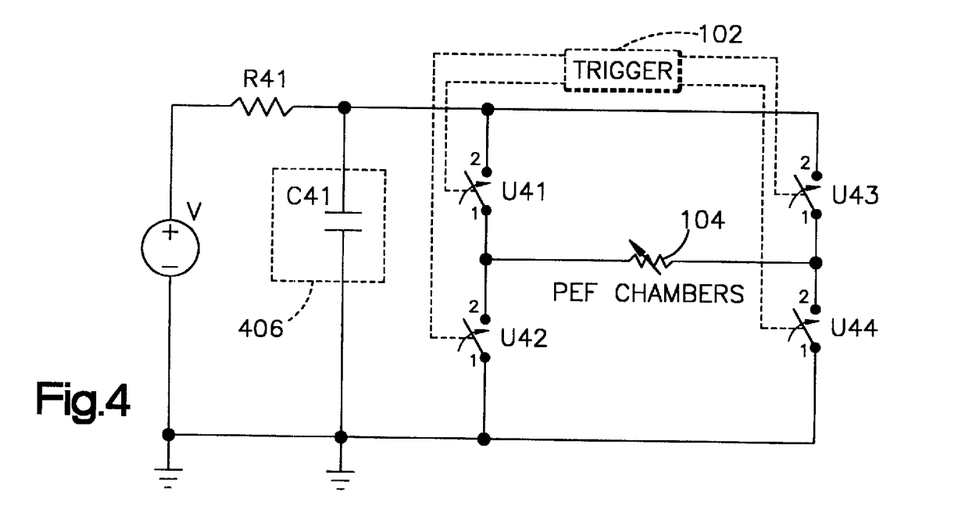
FIG. 4 is the schematic diagram of a fourth embodiment of a high voltage bipolar pulse generator.

Illustrated in FIG. 4 is a fourth embodiment 400 of a high-voltage bipolar pulse generator system of the present invention. The system has a power source V, resistor R41, an energy storage component 406 having capacitor C41, switches U41, U42, U43, and U44, and a load 104 having at least one PEF treatment chamber. The power source V, energy storage capacitor C41 and switches U41–U44 are identical to those used in the third embodiment 300 and operate in the same manner. The load 104 and PEF treatment chambers are connected between two legs (i.e., U41–U42 and U43–U44) of an H-bridge switch configuration, as shown in FIG. 4. The load 104 of PEF treatment chambers is in circuit communication with the switches through a bridge portion of the H-bridge configuration. As described in the embodiment of FIG. 3, periodic closing and opening of the pairs of switches (e.g., U41–U44 and U42–U43), as triggered by trigger device 102, results in the application of bipolar (or unipolar) pulses across the PEF chambers. In the embodiment of FIG. 4, a pulse transformer (shown in embodiment of FIG. 3) is not required if the power source V can provide the desired voltage levels and switches U41–U44 can handle the necessary voltage levels and corresponding switching current levels.

Figure 5:
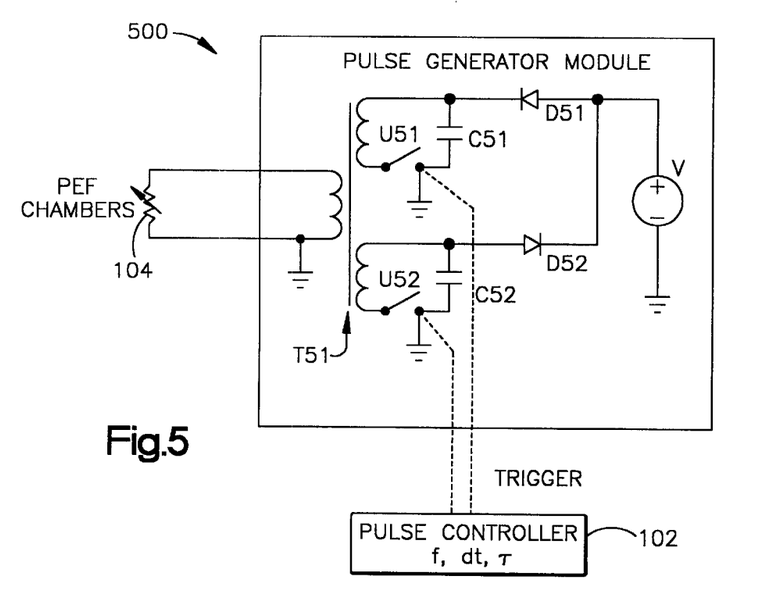
FIG. 5 is the schematic diagram of a fifth embodiment of a high voltage bipolar pulse generator.

Referring now to FIG. 5, a fifth embodiment 500 of the high-voltage bipolar pulse generator system is illustrated. The system has a power source V, an energy storage component having two energy storage capacitors C51 and C52, a set of switches U51 and U52, a pair of diodes D51 and D52, a pulse transformer T51, and a load 104 having one or more PEF treatment chambers. The power source V is similar to the power source used in FIGS. 14. The power source V charges the energy storage capacitors C51 and C52 during alternating charging periods. The two switches U51 and U52 are periodically closed for a short period of time and then opened, as triggered by trigger device 102, to discharge the energy storage capacitors C51 and C52. Each time only one switch (e.g., U51) is involved in discharging its respective energy storage capacitor (e.g., C51) while the other switch remains open (e.g., U52). Switches U51 and U52 are of the type already described in connection with the earlier embodiments.

As described earlier, to generate square wave pulses the capacitance of the energy storage capacitors C51 and C52 should be selected so that a discharge time constant of the circuit shown in FIG. 5 is comparably larger than the time interval between the closing and opening of switches U51 and U52. When the time intervals are larger than five times the discharge time constant, exponential decay pulses are generated and applied to the PEF treatment chambers. If only one of the two switches is closed and opened all the time, high-voltage unipolar pulses, positive or negative in polarity, are generated.

Figure 6:
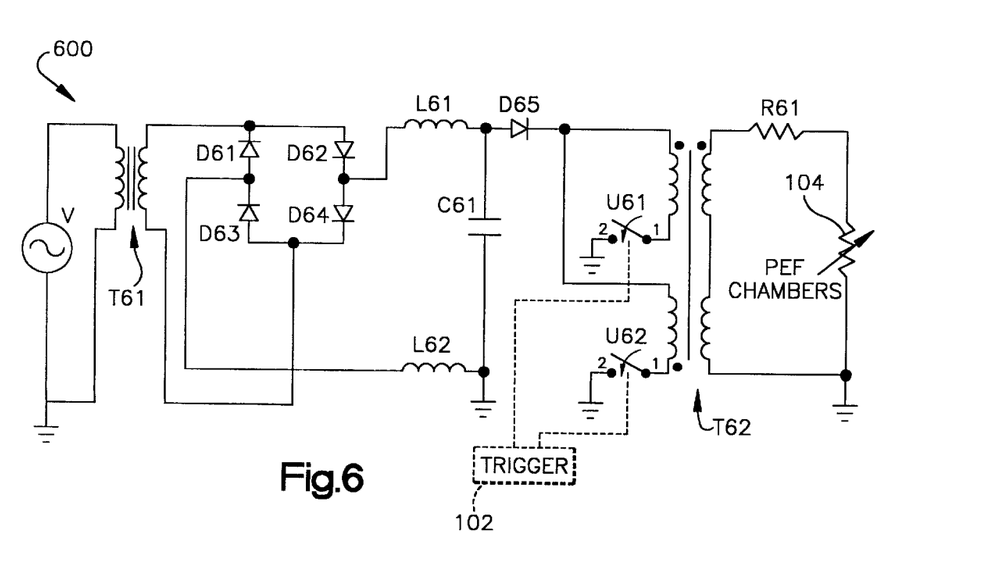
FIG. 6 is the schematic diagram of a sixth embodiment of a high voltage bipolar pulse generator.

Referring now to FIG. 6, a sixth embodiment 600 of the high-voltage bipolar pulse generator system of the present invention is shown. The system has a power source V, isolation transformer T61, diode circuit with four diodes D61, D62, D63, and D64, a pulse forming network having a capacitor C61 and two inductors L61 and L62, a set of switches U61 and U62, diode D65, pulse transformer T62, resistor R61, and a load 104 having one or more PEF treatment chambers. The operation of this embodiment is similar to that of the first embodiment of FIG. 1. Briefly, power source V charges energy storage capacitor C61 through diodes D61–D64 and inductors L61 and L62. Trigger device 102 causes switches U61 and/or U62 to periodically discharge energy storage capacitor C61 through pulse transformer T62 to the PEF treatment chambers of load 104.

Preferably, the present invention is useful in connection with PEF treatment of liquid food product and other pumpable substances wherein high voltage bipolar pulses are used to induce stress and mortality in microorganisms, biological cells, spores, or other particles. However, the present invention can also be used in any application that requires a pulse generator which can maintain high current levels through small resistive loads. Additionally, the present invention can also be used in any application that requires bipolar and/or unipolar high voltage pulses. For example, the high voltage pulse generator of the present invention may be particularly useful in welding applications. The invention also relates to methods of inducing stress and mortality in microorganisms, biological cells, spores, or other particles with PEF's and the novel high voltage pulse generator.

In all of the described embodiments, the high-voltage pulse generator system preferably includes, for example, the following operating characteristics:

| | |
|---|---|
| 1. Operating input voltage: | minimum 120 VAC (alternatively, any standard or nonstandard single or three phase voltage). |
| 2. Operating voltage output: | 0 to 200 kV and preferably 5 to 150 kV. |
| 3. Peak current: | 0 to 50 kA and preferably 10 A to 5 kA. |
| 4. Polarity: | preferably bipolar and/or unipolar. |
| 5. Wave shape: | preferably substantial square wave. |
| 6. Pulse duration: | preferably .5 to 20 microseconds. |
| 7. Output Frequency: | preferably 500 Hz to 20 kHz. |

Figure 7:
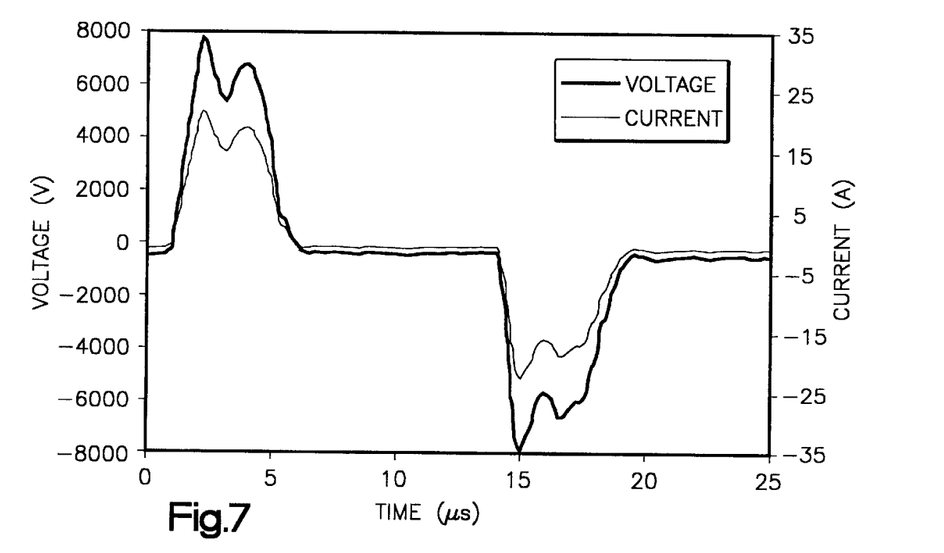
FIG. 7 is the output voltage and current waveforms of the generator shown in FIG. 2. Pulse duration of both positive and negative pulses is 3 μs, delay time in between the two pulses is 12 μs, and load resistance is 400 Ω.
Figure 8:
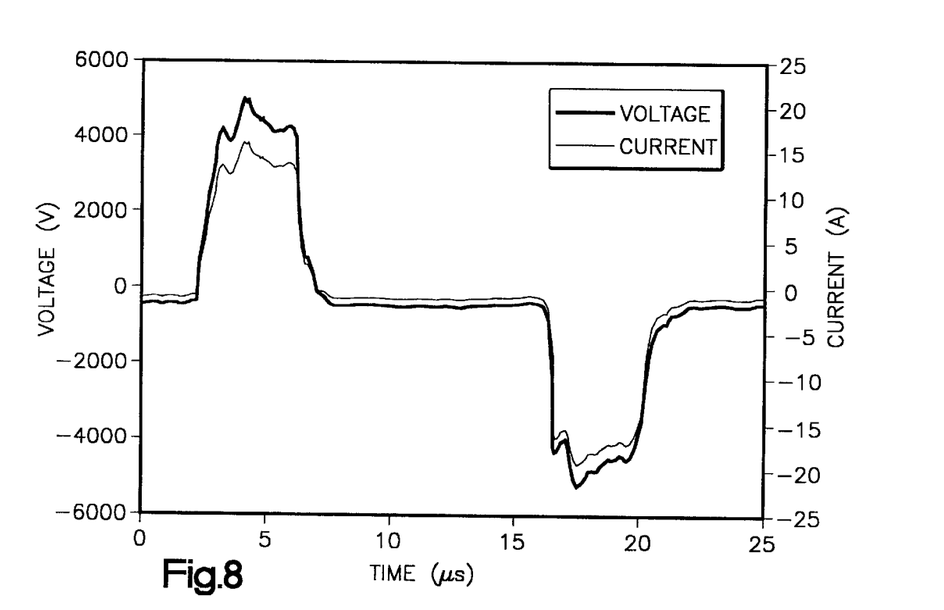
FIG. 8 is the output voltage and current waveforms of the generator shown in FIG. 3. Pulse duration of both the positive and negative pulses is 4 μs, delay time in between the two pulses is 12 μs, and the load resistance is 300 Ω.
Figure 9:
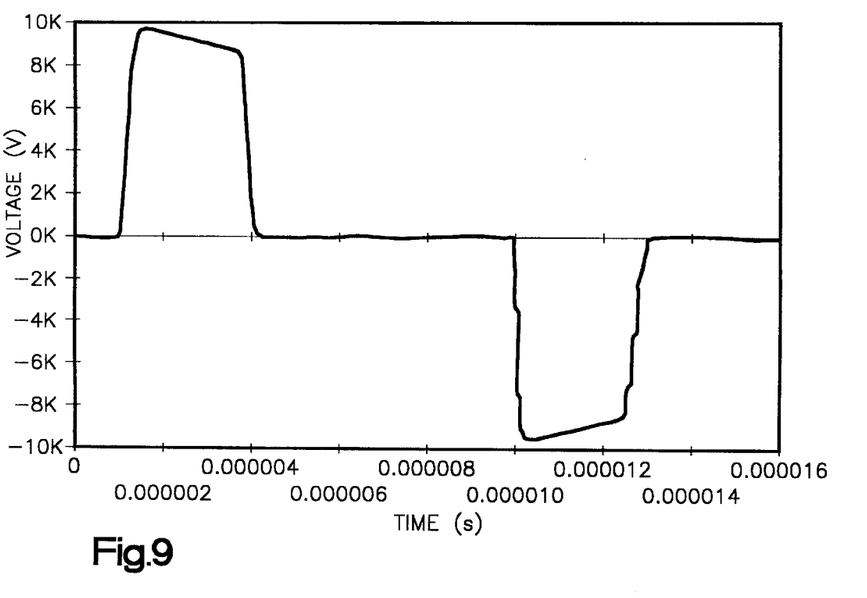
FIG. 9 is the output voltage waveform of the generator shown in FIG. 6.
Figure 10:
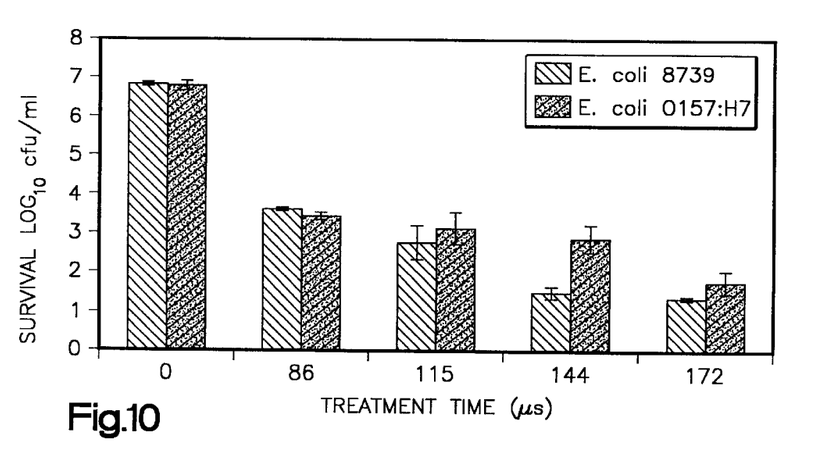
FIG. 10 illustrates the inactivation of *E. coli* 0157:H7 and *E. coli* 8739 in apple juice samples by PEF treatment.

FIG. 7 is the output voltage and current waveforms of the generator shown in FIG. 2. Pulse duration of both positive and negative pulses is 3 $\mu$s, delay time in between the two pulses is 12 $\mu$s and the load resistance is 400 $\Omega$. FIG. 8 illustrates the output voltage and current waveforms of the generator shown in FIG. 3. Pulse duration of both the positive and negative pulses is 4 $\mu$s, delay time in between the two pulses is 12 $\mu$s, and the load resistance is 300 $\Omega$. FIG. 9 is the output voltage and current waveforms of the generator shown in FIG. 6. FIG. 10 illustrates the inactivation of *E. coli* 0157: H7 and *E. coli* 8739 in apple juice samples by the PEF treatment of the present invention.

While the present invention has been illustrated by the description of embodiments thereof, and while the embodiments have been described in considerable detail, it is not the intention of the applicants to restrict or in any way limit the scope of invention to such detail. Additional advantages and modifications will readily appear to those skilled in the art. For example, the waveforms may sloped or rounded pulses. Therefore, the invention, in its broader aspects, is not limited to the specific details, the representative apparatus, and illustrative examples shown and described. Accordingly, departures may be made from such details without departing from the spirit or scope of the applicant's general inventive concept.

We claim:

1. A system for generating high-voltage bipolar pulses to induce stress and mortality in biological cells, the system comprising:

(a) a power source;

(b) an energy storage component in circuit communication with the power source and for storing energy from the power source;

(c) a plurality of switches for opening and closing periodically to discharge the energy storage component through a pulse transformer to a load; and (d) the load comprising at least one Pulse Electric Field (PEF) treatment chamber in which biological cells are subjected to PEF treatment.

2. The system of claim 1 wherein the pulse transformer is in circuit communication with the energy storage component and the load and allows for a plurality of voltage and current levels to be generated at the load.

3. The system of claim 1 wherein the energy storage component comprises at least one capacitor such that the energy storage component has a discharge time constant that is larger than the time interval between the closing and opening of the switches.

4. The system of claim 1 wherein the plurality of switches comprise at least a first switch and a second switch and wherein the first and second switches are sequentially opened and closed.

5. The system of claim 4 wherein the energy storage component comprises a first and second energy storage device, wherein the first energy storage device is associated with the first switch and the second energy storage device is associated with the second switch.

6. The system of claim 1 further comprising a trigger device in circuit communication with the plurality of switches and for triggering the switches between an opened state and a closed state.

7. The system of claim 6 wherein the plurality of switches comprise at least first, second, third, and fourth switches and wherein said switches are configured to operate in pairs.

8. The system of claim 1 further comprising a trigger device in circuit communication with the plurality of switches and for triggering the switches between an opened state and a closed state.

9. The system of claim 1 wherein the load is in circuit communication with said switches through a bridge portion of the H-bridge configuration.

10. A system for generating high-voltage bipolar pulses to induce stress and mortality in biological cells, the system comprising:

(a) a power source;

(b) an energy storage component in circuit communication with the power source and for storing energy from the power source, said energy storage component comprising a single capacitor;

(c) a plurality of switches for opening and closing periodically to discharge the energy storage component through a pulse transformer to a load; and (d) the load comprising at least one Pulse Electric Field (PEF) treatment chamber in which biological cells are subjected to PEF treatment.

11. The system of claim 10 wherein the pulse transformer is in circuit communication with the energy storage component and the load and allows for a plurality of voltage and current levels to be generated at the load.

12. The system of claim 10 wherein the capacitor has a discharge time constant that is larger than the time interval between the closing and opening of the switches.

13. The system of claim 10 wherein the plurality of switches comprise at least a first switch and a second switch and wherein the first and second switches are sequentially opened and closed.

14. The system of claim 10 further comprising a trigger device in circuit communication with the plurality of switches and for triggering the switches between an opened state and a closed state.

15. A system for generating high-voltage bipolar pulses to induce stress and mortality in biological cells, the system comprising:

(a) a power source;

(b) an energy storage component in circuit communication with the power source and for storing energy from the power source;

(c) a plurality of switches for opening and closing periodically to discharge the energy storage component through a pulse transformer to a load, wherein the plurality of switches are configured in an H-bridge configuration; and (d) the load comprising at least one Pulse Electric Field (PEF) treatment chamber in which biological cells are subjected to PEF treatment.

16. The system of claim 15 wherein the pulse transformer is in circuit communication with the energy storage component and the load and allows for a plurality of voltage and current levels to be generated at the load.

17. The system of claim 15, wherein the energy storage component comprises at least one capacitor such that the energy storage component has a discharge time constant that is larger than the time interval between the closing and opening of the switches.

* * * * *